US010179871B2

(12) United States Patent
Lammerschop et al.

(10) Patent No.: US 10,179,871 B2
(45) Date of Patent: Jan. 15, 2019

(54) TWO-COMPONENT BINDER SYSTEM WITH CYCLOCARBONATE AND EPOXY GROUPS

(71) Applicant: Henkel AG & Co. KGaA, Duesseldorf (DE)

(72) Inventors: Olaf Lammerschop, Krefeld (DE); Hans-Georg Kinzelmann, Pulheim (DE); Therese Hemery, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/279,504

(22) Filed: Sep. 29, 2016

(65) Prior Publication Data
US 2017/0015883 A1    Jan. 19, 2017

Related U.S. Application Data

(63) Continuation of application No. PCT/EP2015/057367, filed on Apr. 2, 2015.

(30) Foreign Application Priority Data

Apr. 4, 2014  (DE) .................. 10 2014 206 574

(51) Int. Cl.
| C08L 75/12 | (2006.01) |
| C09J 175/04 | (2006.01) |
| C07D 317/36 | (2006.01) |
| C08G 71/00 | (2006.01) |
| C08G 71/04 | (2006.01) |
| B32B 7/12 | (2006.01) |
| B65D 65/40 | (2006.01) |
| C08J 7/04 | (2006.01) |

(52) U.S. Cl.
CPC .............. *C09J 175/04* (2013.01); *B32B 7/12* (2013.01); *B65D 65/40* (2013.01); *C07D 317/36* (2013.01); *C08G 71/00* (2013.01); *C08G 71/04* (2013.01); *C08J 7/047* (2013.01); *C08L 75/12* (2013.01); *B32B 2439/70* (2013.01); *C08J 2375/04* (2013.01)

(58) Field of Classification Search
None
See application file for complete search history.

(56) References Cited

U.S. PATENT DOCUMENTS

| 3,624,016 | A | 11/1971 | Lew |
| 4,485,211 | A | 11/1984 | Okamoto |
| 4,751,273 | A | 6/1988 | Lapin et al. |
| 4,835,289 | A | 5/1989 | Brindopke |
| 4,892,954 | A | 1/1990 | Brindopke et al. |
| 5,132,458 | A | 7/1992 | Honel et al. |
| 5,200,490 | A | 4/1993 | Jaeger et al. |
| 5,384,342 | A | 1/1995 | Szum |
| 5,539,014 | A | 7/1996 | Swedo et al. |
| 5,677,384 | A | 10/1997 | Detering et al. |
| 5,977,266 | A | 11/1999 | Reil et al. |
| 6,407,198 | B1 | 6/2002 | Figovsky et al. |
| 6,495,637 | B2 | 12/2002 | Rappoport |
| 6,627,761 | B2 | 9/2003 | Klein et al. |
| 7,232,877 | B2 | 6/2007 | Figovsky et al. |
| 8,118,968 | B2 | 2/2012 | Moeller et al. |
| 2010/0022706 | A1* | 1/2010 | Jenninger .............. C08G 18/10 524/590 |
| 2012/0035381 | A1 | 2/2012 | Klumpe et al. |

FOREIGN PATENT DOCUMENTS

| AU | 2012219869 A1 | 9/2013 |
| CN | 102558491 A | 7/2012 |
| DE | 3529263 A1 | 2/1987 |
| DE | 3600602 A1 | 7/1987 |
| DE | 4109649 A1 | 9/1992 |
| DE | 102004035542 A1 | 2/2006 |
| EP | 0303158 A2 | 2/1989 |
| EP | 0328150 A2 | 8/1989 |
| EP | 1020457 A1 | 7/2000 |
| JP | H07224131 A | 8/1995 |
| RU | 2100377 C1 | 12/1997 |
| WO | 8403701 A1 | 9/1984 |
| WO | 9429422 A1 | 12/1994 |
| WO | 9850345 A1 | 11/1998 |
| WO | 2012113618 A1 | 8/2012 |
| WO | WO 2014/158705 A1 * | 10/2014 |

OTHER PUBLICATIONS

International Search Report for International PCT Patent Application No. PCT/EP2015/057367 dated Jul. 3, 2015.
Henry Lee and Kris Neville, Handbook of Epoxy Resins, chapter 7, pp. 7-1 to 7-33 McGrawHill Book company New York 1967.

(Continued)

*Primary Examiner* — Ana L. Woodward
(74) *Attorney, Agent, or Firm* — James E. Piotrowski

(57) ABSTRACT

The present invention relates to a binder system containing a resin component and a curing agent component, wherein the resin comprises at least one compound carrying at least two cyclic carbonate groups and at least one compound carrying at least two epoxy groups, and the curing agent comprises at least one multifunctional amine as well as the use of the binder system as an adhesive/sealant and the use of this adhesive/sealant.

22 Claims, No Drawings

(56) References Cited

OTHER PUBLICATIONS

Clayton A. May, Epoxy Resins, pp. 466-469, Marcel Dekker, New York 1988.
Henry Lee and Kris Neville, Handbook of Epoxy Resins, chapter 10, pp. 10-1 to 10-23 McGrawHill Book company New York 1967.
Matyjaszewski, K. Hrsg., Cationic Polymerizations: Mechanisms, Synthesis, and Applications (in: Plast. Eng. (N. Y.), 1996, 35, Dekker.
M. Sangermano, N. Razza and J. V. Crivello (Macromol. Mater. Eng., 2014, 299, S. 775-793).
PEG-based Multifunctional Polyethers with Highly Reactive Vinyl-Ether Side Chains for Click-Type Functionalization; Macromolecules vol. 44, Issue: 16, pp. 6326-6334.
Kayaman-Apohan et al., Synthesis and characterization of UV-curable vinyl ether functionalized urethane oligomers, Progress in Organic Coatings 49 (2004), 23-32.

\* cited by examiner

TWO-COMPONENT BINDER SYSTEM WITH CYCLOCARBONATE AND EPOXY GROUPS

The present invention relates to a binder system comprising a resin component and a curing agent component, wherein the resin contains at least one compound having at least two cyclic carbonate groups and at least one compound having at least two epoxy groups, and the curing agent comprises at least one multifunctional amine as well as the use of the binder system as an adhesive/sealant and the use of this adhesive/sealant.

Two-component binder systems, in particular those based on polyols and NCO-terminated compounds, have long been known in the state of the art. They are used as adhesives, sealing compounds, fillers or casting compounds (casting), for example, in the field of the metalworking industry, the automotive industry, the electronics industry, the packaging industry or the construction industry. One disadvantage of the polyurethanes having NCO groups that are used as the so-called resin is their sensitivity to moisture. Therefore, tight containers must be used accordingly when storing these compounds. Once a container has been opened, it must be consumed immediately in most cases, i.e., within a short period of time, to avoid a loss of quality. The polyol component must also be dried carefully in most cases before being mixed with the resin component because otherwise a residual amount of moisture can lead to unwanted blistering in the adhesive film, which causes disadvantages in final application under some circumstances. Another disadvantage of at least some binder systems based on two-component polyurethane adhesives is the toxicology of monomeric isocyanates, in particular readily volatile and/or readily migrating monomeric isocyanates, in the resin component. The use of products containing a large amount of readily volatile diisocyanates requires extensive occupational safety measures on the part of the user, in particular complex measures for keeping the respiratory air clean, as prescribed by law, due to the maximum allowed concentration of occupational substances in the form of a gas, vapor or particulate matter suspended in the air at the job site (MAC—Maximum Allowed Concentration—list, updated annually, of the Technical Rule TRGS 900 of the Federal Ministry of Labor and Social Affairs).

However, free monomeric polyisocyanates can also "migrate" into the coating or bonding or to some extent may also migrate into the coated or glued materials. Such migrating components are often referred to in technical circles as "migrates." Through contact with moisture, the isocyanate groups of the migrates are converted continuously to amino groups.

In the packaging field, in particular in food packagings, migrates are particularly unwanted. On the one hand, the migration of the migrates through the packaging material can result in contamination of the packaged material. On the other hand, long waiting times are necessary before the packaging material is "migrate-free" and may be used, depending on the amount of free monomeric polyisocyanate that can migrate.

Another unwanted effect that may be caused by migration of monomeric polyisocyanates is the so-called anti-sealing effect in the production of bags or packets of laminated plastic films: the laminated plastic films often contain lubricants based on fatty acid amides. By reaction of migrated monomeric polyisocyanate with fatty acid amide and moisture, urea compounds that are formed on the surface of the film have a melting point which may be higher than the sealing temperature of the plastic films. This results in an atypical anti-sealing layer between the film parts to be sealed, counteracting a uniform sealing seam formation.

Products based on compounds containing cyclic carbonate groups and aliphatic polyamines are known in principle from WO 2006/010408, for example. Although the products described therein overcome the aforementioned disadvantages, while at the same time having good adhesive/sealing properties, they also require high curing temperatures of at least 80° C., with the average tending to be around 100° C. which is a disadvantage for certain applications or may even make them impractical. However, at lower temperatures, such as 40° C., for example, curing is incomplete and adhesion later is too low.

The object of the present invention was therefore to make available a binder system that would overcome these disadvantages and would enable adequate curing even at low temperatures and would exhibit good adhesion properties.

The inventors have surprisingly found that this object can be achieved by a binder system and that an epoxy resin component can be used in addition to a resin component containing cyclic carbonate groups. The binder systems obtained in this way exhibit complete curing at temperature of 40° C. with adhesion properties comparable to those of known systems.

In a first aspect, the invention therefore relates to a binder system containing the components (A) and (B), wherein component (A) comprises at least one compound having at least two cyclic carbonate groups and at least one compound having at least two epoxy groups; and component (B) comprises at least one compound having at least two (—NHR—) atomic groups, wherein R is H, an alkyl or aryl radical. The alkyl radical may be linear or branched, saturated or mono- or polyunsaturated, substituted or unsubstituted and has in particular 1 to 30 carbon atoms. The aryl radical may be monocyclic or polycyclic, substituted or unsubstituted and has 6 to 22 carbon atoms in particular.

In another aspect, the invention relates to methods for producing an adhesive/sealant using the binder system described herein. In this variant the component (A) is mixed with component (B) in a ratio of carbonate groups to primary amino groups of 30:1 to 0.2:1, preferably 10:1 to 0.4:1, more preferably 5:1 to 0.5:1, especially preferably 2:1 to 0.6:1, in particular preferably 1.1:1 to 0.9:1 and most preferably approx. 1:1. IN the absence of primary amino groups, this mixing ratio is to be applied to secondary amino groups.

In yet another aspect, the invention relates to the use of the binder system described herein as a two-component adhesive for adhesive bonding of paper, cardboard, wood, plastic, metal or stoneware, in particular as a solvent-free or solvent-containing lamination adhesive or for producing casting compounds.

Finally the invention also relates to methods for producing film laminates, wherein at least two plastic films that are the same or different are bonded together over all or part of the surface using a binder system described herein, as well as the film composite produced in this way.

The molecular weights given in the present text refer to the weight-average molecular weight (Mw), unless otherwise indicated. All molecular weight specifications refer to values such as those obtained by gel permeation chromatography (GPC) according to the standard DIN 55672-1: 2007-08 unless otherwise indicated.

"At least one," as used here denotes one or more, i.e., 1, 2, 3, 4, 5, 6, 7, 8, 9 or more. Based on one ingredient, this specification refers to the type of ingredient and not the absolute number of molecules. "At least one polyol" thus denotes, for example, at least one type of polyol, i.e., a type of polyol or a mixture of several different polyols may be used. Together with weight specifications, the specification refers to all compounds of the stated type, which are contained in the composition/mixture, i.e., the composition does not contain any other compounds of this type beyond the specified amount of the corresponding compounds.

All percentage amounts specified in conjunction with the compositions described herein refer to % by weight (wt. %), unless otherwise indicated, always based on the respective mixture.

"Approximately" or "approx." as used herein in conjunction with a numerical value refers to the numeral value ±10%, preferably ±5%, It has, surprisingly, been found that the binder systems described herein have an essentially complete conversion even at comparatively low temperatures, are suitable as adhesives/sealants and are characterized by a good adhesion to surfaces of a wide variety of materials. The essentially NCO group-free polyurethane adhesives/sealants may be used in substance or in solution in conventional organic solvents. "Essentially free of NCO groups" means that the NCO content in components (A) <0.1% by weight (determined according to Spiegelberger, EN ISO 1909:2007-05).

Any polymers may be used as the at least one compound having at least two cyclic carbonate groups as long as they do not have any other functional groups which could interfere with the reaction with component (B). The at least one compound containing at least two cyclic carbonate groups may be both linear and branched. As already mentioned, the term "at least one" in this context means that the binder system may contain one or more compounds, each of which has at least two cyclic carbonate groups. "At least two cyclic carbonate groups" means that the compounds have two or more but preferably exactly two cyclic carbonate groups, in particular terminal groups.

The cyclic carbonate groups are preferably disposed on the polymer chain ends but in many cases it is also possible to use compounds containing these groups in random distribution over the entire polymer chain. The cyclic carbonate groups may thus be built into the main chain as well as being disposed in a side position.

The compound having at least two cyclic carbonate groups is preferably a polymer, the polymer being selected from the group of fat chemical compounds, polyethers, polyether polyols, polyesters, polyester polyols, polycarbonates, polycarboxylic acids, polyacrylates, polymethacrylates, polyamides, polyamines, polyurethanes or mixtures thereof. The preferred fat chemical compounds include castor oil or dimer diol which are also alkoxylated. Especially preferred within the context of this invention are polyurethanes.

Polyamides are understood to be those which do not have any amine NH groups.

Cyclocarbonates, which may also be referred to as cyclic carbonates, are to be understood as structures in which a carbonic acid ester group is part of a ring structure according to formula (I):

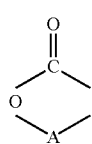

(I)

wherein

A is $(C(R^1R^2))_n$, where n>2, preferably n=2 or 3, in particular preferably n=2; $R^1$, $R^2$ are each selected independently of one another from hydrogen, a saturated or unsaturated, linear or branched or cyclic aromatic or aryl aliphatic, optionally substituted hydrocarbon radical with 1 to 12 carbon atoms, an ether radical with 1 to 12 carbon atoms and up to three oxygens, $R^3X$, where $R^3$ is a divalent aliphatic, cycloaliphatic aromatic aryl aliphatic or ether-containing, optionally substituted hydrocarbon radical with 1 to 20 carbon atoms and X is a hydroxy, epoxy, carboxylic acid or carboxylic acid ester group, or Z, wherein Z is an unsaturated polymerizable group, in particular a vinyl, (meth)acryl, maleic acid, fumaric acid, itaconic acid or crotonic acid ester group.

Specific examples of cyclocarbonates include, without being limited to, ethylene carbonate (1,3-dioxolan-2-one); propylene carbonate (4-methyl-1,3-dioxolan-2-one); glycerin carbonate (4-methylhydroxy-1,3-dioxolan-2-one); 5-ethyl-5-(hydroxymethyl)-1,3-dioxan-2-one; 1,3-dioxan-2-one, 5-(allyloxy)methyl)-5-ethyl-1,3-dioxan-2-one or 1,3-dioxepin-2-one. Cyclic carbonates having epoxy groups are described in DE 3726497 A1, for example.

Cyclic carbonates are obtained, for example, by transesterification of carbonic acid esters such as, for example, dimethyl carbonate, diethyl carbonate, diphenyl carbonate, ethylene carbonate or propylene carbonate with polyols, wherein the polyols preferably have at least three hydroxyl groups, two of which react with carbonic acid esters in a transesterification reaction to form cyclic five-membered or six-membered carbonates. Examples of polyvalent polyols that can be mentioned include glycerol, diglycerol, triglycerol, polyglycerol, sugar alcohols (for example, xylitol, mannitol, erythritol), di- and trimethylolpropane, di- and trimethylolethane, pentaerythritol, dipentaerythritol. Glycerol is especially preferred here. The cyclic carbonates are synthesized from the polyols by methods with which those skilled in the art are familiar, in particular by reacting the polyols with the carbonates in a stoichiometric ratio of 1.0:1.0 to 1.0:10.0 (ratio of 1,2- or 1,3-glycol groups to form carbonate groups), in particular with catalysis. Examples of suitable catalysts include basic catalysts such as, for example, carbonates, bicarbonates, alcoholates, carboxylates, hydroxides or oxides of the alkali and alkaline earth metals as well as Lewis acid substances, for example, organic compounds of divalent or trivalent tin or titanium, for example, tin(II) octoate, tin(II) laureate, dibutyltin oxide or titanium tetrabutylate. The catalysts may be added in an amount of 0.01 to 1.0% by weight, based on polyol and carbonic acid esters, for example.

Cyclic carbonates can also be obtained by reacting carbon dioxide with epoxy compounds in the known manner. Conversion reactions are described, for example, in WO 84/03701, DE-A 3529263 or DE-A 3600602.

By reacting polyols with phosgene, both aliphatic and aromatic cyclic carbonates can be obtained (e.g., U.S. Pat. No. 3,624,016).

Furnishing the polymer with at least two cyclic carbonate groups, hereinafter referred to as functionalization, may take place during the synthesis of the polymer chain, wherein corresponding monomer building blocks containing cyclocarbonate groups may be used. However, it is preferable to subsequently functionalize a polymer that has already been synthesized. Especially preferred here is addition of cyclic hydroxyalkyl carbonates onto polymers having anhydride groups or isocyanate groups. In principle, a corresponding method is described in EP 0328150 A2. Cyclic hydroxyalkyl carbonates with five-membered or six-membered carbonate rings are preferred for use in the addition reaction. Glycerin carbonate is most especially preferred. It is likewise possible to react such cyclic hydroxyalkyl carbonates by transesterification, in which $C_1$-$C_4$ alkyl ester groups of the polymer, for example, may be reacted directly or it is possible to react hydroxyl groups of the polymers with an ester groups of a low-molecular $C_2$ to $C_6$ dicarboxylic acid ester and then react the remaining $C_1$-$C_4$ alkyl ester groups with a hydroxyalkyl carbonate. Low-molecular dicarboxylic acid esters are understood to be those in which the dicarboxylic acid radical is constructed from 2 to 44 carbon atoms, preferably 2 to 12 carbon atoms, especially preferably 2 to 6 carbon atoms and may have a linear or branched aliphatic, cycloaliphatic or aromatic structure. Another possibility for inducing hydroxyalkyl carbonates to react is their reaction with acid halides, in particular carboxylic acid halides.

In another embodiment of the invention, examples of compounds having at least two cyclic carbonate groups include those obtained by addition of carbon dioxide onto polymers containing epoxy groups. In principle, such an addition method is described in Unexamined German Publications DE-OS 3529263 and/or DE-OS 3600602.

Due to the choice of the basic compound and the choice of the functionalization with the cyclic carbonate groups, it is possible to obtain polymers containing urethane groups or only ester groups. It is possible in this way to influence the viscosity of the polymer.

Polyurethanes functionalized with at least two cyclic carbonate groups are preferred. The cyclic carbonate groups are arranged at the termini in particular. Such functionalized polymers are produced in a two-step synthesis. In a first step, a polyol or a polyol mixture with a stoichiometric excess of polyisocyanate is reacted to obtain an NCO-terminated polyurethane prepolymer, which is then functionalized with the cyclic carbonate groups in a second step, for example, by reacting a cyclic hydroxyalkyl carbonate, in particular one having a five-membered or six-membered carbonate ring, most especially preferably glycerin carbonate, with the terminal isocyanate groups.

It is therefore preferable for the compound having at least two cyclic carbonate groups to be the reaction product of a polymer containing an isocyanate group, in particular an isocyanate group-terminated polyurethane prepolymer with a hydroxyalkyl carbonate, in particular one having a five-membered or six-membered carbonate ring, most especially preferably glycerin carbonate.

The polyols used in the synthesis of the polymer may all be the polyols generally used for polyurethane synthesis, for example, polyester polyols or polyether polyols, in particular polyether polyols such as polypropylene glycol or polyethylene glycol. The polyols used preferably have an average molecular weight (Mw) of 60 to 4000 g/mol, preferably 75 to 2000 g/mol.

The polyisocyanates used are in particular diisocyanates, especially preferably aromatic diisocyanates. Example of suitable diisocyanates include methylene diphenyl diisocyanates (MDI) such as 4,4'-methylene diphenyl diisocyanate, 2,4'-melthylene diphenyl diisocyante or 2,2'-methylene diphenyl diisocyanate as well as mixtures thereof.

The at least one compound having at least two cyclic carbonate groups is therefore preferably a cyclocarbonate-terminated polyurethane prepolymer of a polyether polyol and an aromatic diisocyanate such as MDI.

The molecular weight (Mw) of the at least one compound having at least two cyclic carbonate groups is preferably from 1500 g/mol to 100,000 g/mol, in particular preferably 2000 g/mol to 50,000 g/mol.

In a further embodiment, a further low-molecular compound containing cyclic carbonate groups may also be present in the bonder system. This component should have a molecular weight (Mw) <1000 g/mol, preferably <800 g/mol and should contain at least two cyclic carbonate groups. These may be, for example, diepoxies reacted with $CO_2$ or di- or tricarboxylic acid esters that have been reacted at the ester groups with the aforementioned hydroxy-functional cyclic carbonates. Components of this type are also referred to as reactive diluents and may be added in amounts of up to 60% by weight, preferably up to 25% by weight, based on (A) to influence the viscosity of the binder system.

Component (A) additionally contains at least one compound having at least two epoxy groups. The compounds that can be used herein are preferably epoxy resins, for example, polyglycidyl epoxy compounds or epoxy novolacs. Suitable polyglycidyl epoxies include, without being limited to, polyglycidyl ethers, poly(β-methylglycidyl) ethers, polyglycidyl esters and poly(β-methylglycidyl)esters and mixtures of the aforementioned epoxy resins. Suitable polyglycidyl ethers or esters include, for example, diglycidyl ethers or esters of aliphatic diols or dicarboxylic acids. Also suitable are cycloaliphatic epoxy resins such as, for example, (di)ethers or (di)esters based on 3,4-epoxycyclohexylmethanol.

The at least one epoxy resin is selected from various embodiment from diglycidyl ethers based on propylene glycol or ethylene glycol.

It is preferred in general for the compound having at least two epoxy groups to be an aliphatic epoxy. Epoxies having an epoxy equivalent weight (EEW, epoxy equivalent weight) of 100 to 500 g/mol, preferably 120 to 350 g/mol are preferred. The EEW refers to the weight of epoxy compound containing 1 mol epoxy groups. It can be determined according to the standard DIN EN ISO 3001:1999-11.

The amount of epoxy in component (A) is preferably 5 to 30% by weight, based on the total amount of solids (cyclocarbonate compound and epoxy). Accordingly, the cyclocarbonate compound is present in an amount of 70 to 95% by weight, based on the total amount of solids.

In addition to component (A), the binder system according to the invention contains at least one multifunctional amine, i.e., at least one compound having at least two (—NHR—) atomic groups or a mixture of two or more compounds having at least two (—NHR—) atomic groups as component (B), where R=H, alkyl or aryl radical.

The compounds of component (B) may be both linear and branched. The molecular structure of component (B) may contain aliphatic, aromatic, aliphatic aromatic, cycloaliphatic and heterocyclic structures. Primary and/or secondary and tertiary amines may be present in the molecule, but at least two (—NHR—) atomic groups must be present, preferably two amino groups. The amine functions per se are aliphatic, i.e., the carbon atoms directly vicinal to the amine nitrogen are not part of an aromatic ring structure.

Component (B) preferably contains a multifunctional amine as component (B1), in particular having a molecular weight (Mw) of 60 g/mol to 500 g/mol, preferably from 60 g/mol to 300 g/mol and/or a multifunctional amine as component (B2), in particular with an average molecular weight (Mw) of >500 g/mol. Mixtures of (B1) and (B2) are especially preferred. The weight ratio of (B1) to (B2) in the mixtures of (B1) with (B2) that are used is 0.5:20 to 20:0.5.

The upper limit of the molecular weight (Mw) of component (B2) is approx. 5,000,000 g/mol. Component (B2) preferably has an average molecular weight (Mw) of 600 g/mol to 20,000 g/mol, in particular preferably 800 g/mol to 2000 g/mol.

Component (B1) is used as a single component or as a mixture of the corresponding compounds that can be used as component (B1). Component (B1) is preferably selected from the group of alkylene diamines and/or cycloalkylene diamines.

Alkylene diamines are understood to be compounds of the general formula $R^4R^5N—Z—NR^6R^7$ in which $R^4$, $R^5$, $R^6$ and $R^7$, independently of one another, may be H, alkyl or cycloalkyl radicals. Z denotes a linear or branched, saturated or unsaturated alkylene chain having two or preferably more than two carbon atoms. Preferred examples include diaminoethane, diaminopropane, 1,2-diamino-2-methylpropane, 1,3-diamino-2,2-dimethylpropane, diaminobutane, diaminopentane, 1,5-diamino-2-methylpentane, neopentyl diamine, diaminohexane, 1,6-diamino-2,2,4-trimethylhexane, 1,6-diamino-2,4,4-trimethylhexane, diaminoheptane, diaminooctane, diaminononane, diaminodecane, diaminoundecane, diaminododecane, dimer amine (known commercially, for example, under the brand names Versamin 551 from Cognis and/or BASF), triacetone diamine, dioxadecane diamine, N,N-bis(3-aminopropyl)dodecylamine (available commercially, for example, under the brand name Lonzabac 12.30 from Lonza) or mixtures thereof.

Cycloalkylene diamines are to be understood as compounds of the general formula $R^8R^9N—Y—NR^{10}R^{11}$, in which $R^8$, $R^9$, $R^{10}$ and $R^{11}$ independently of one another may be H, alkyl or cycloalkyl radicals. Y denotes a saturated or unsaturated cycloalkyl radical with more than three carbon atoms, preferably more than four carbon atoms. Diaminocyclopentanes, diaminocyclohexanes, diaminocycloheptanes, for example, 1,4-cyclohexanediamine, 4,4'-methylene-biscyclohexylamine, 4,4'-isopropylene-biscyclohexylamine, isophorone diamine, m-xylylene diamine, N-aminoethylpiperazine or mixtures thereof.

The diamines may also contain both alkyl radicals and cycloalkyl radicals together. Preferred examples include aminoethylpiperazine, 1,8-diamino-p-menthane, isophorone diamine, 1,2-(bisaminomethyl)cyclohexane, 1,3-(bisaminomethyl)cyclohexane, 1,4-(bisaminomethyl)cyclohexane and bis-(4-aminocyclohexyl)methane.

Additional examples of diamines that can be used for component (B1) according to the invention include bis-(6-aminohexyl)amine, α,α'-diaminoxylols, etc.

Highly functional amines are preferably used as component (B1) and/or component (B2). In particular these are the amino-functionalized polyalkylene glycols, such as 1,2-bis-(aminoethoxy)ethane, 1,13-diamino-4,7,10-trioxatridecane. Amine-functionalized polyalkylene glycols that can be used according to the invention include those available commercially as Jeffamine® from Huntsman Corp. The preferred Jeffamines are D-230, D-400, D-2000, D-4000, T-403, T-3000, T-5000, ED-600, ED-2003.

Polyfunctional amines that can also preferably be used as component (B1) and/or component (B2) are compounds of the general formula $H_2N—(CH_2CH_2—NH)_x—CH_2CH_2—NH_2$, where $1<x<10$ such as diethylenetriamine, triethylenetetramine, tetraethylenepentamine, pentaethylenehexamine, dipropylenetriamine, bis-(3-aminopropyl)amine, N,N-bis(3-aminopropyl)ethylenediamine, bishexamethylenetriamine, heptaethyleneoctamine and the like.

Polymers selected from the group consisting of polyamines, polyimines, polyethers, polyamides, polyaminoamides, polyurethanes, polyolefins, polyvinyl amines or mixtures thereof are preferred for use as component (B2).

Polyamines that can be used as component (B2) are described by Henry Lee and Kris Neville, *Handbook of Epoxy Resins*, chapter 7, pages 7-1 to 7-33, McGraw-Hill Book Company, New York 1967 and the literature cited there as well as by Clayton A. May, *Epoxy Resins*, pages 466-468, Marcel Dekker, New York 1988 and the literature cited there.

Preferred polyimines include polyethyleneimines. The amine hydrogen functions of the polyethyleneimines may also be partially modified such as, for example, by alkylation, benzylation, acylation, alkoxylation, preferably ethoxylation and/or propoxylation. Modification with epichlorohydrin is particularly preferred. Polyethyleneimines that can preferably be used are available commercially from BASF under the brand names Lupasol® PS, P, WF, Bo 150, FC, FG, G100, G-20, G-35, G-500, HF, PO-100, PR-8515 and SK or as obtained from DOW under the brand names Polyethylenimin 6, 12, 18, 600 and 1000.

Polyaminoamides contain both amine and amide functionalities in the main chain. Polyaminoamides are synthesized by polycondensation of polyamines and dicarboxylic acids or by Michael addition of acrylic acid esters onto diamines and subsequent polycondensation of the resulting amine acid esters. Polyaminoamides that can be used as component (B2) are described by Henry Lee and Kris Neville, *Handbook of Epoxy Resins*, chapter 10, pages 10-1 to 10-23, McGraw-Hill Book Company, New York 1967 as well as by Clayton A. May, *Epoxy Resins*, pages 469, Marcel Dekker, New York 1988 and the literature cited there.

Within the scope of the present invention, polyaminoamides that are obtained by polycondensation of aliphatic polyamines and dimerized or trimerized fatty acids are preferably used. Grafted and ungrafted polyaminoamides such as those described in WO 94/29422 may also be used. Polyaminoamides from Cognis and/or BASF are commercially available under the brand names Versamid® from Bakelite AG under the brand names Ruetadur or the company S.I.Q. Kunstharz GmbH from the SIQTherm product series.

Additional polyamines that can preferably be used as component (B2) include polyvinylamines. Polyvinylamines may be synthesized, for example, by polymerization of N-vinylacylamines such as N-vinylformamide, N-vinylacetamide, etc. and subsequent complete or partial hydrolysis of the amide group. Polyvinylamines that may preferably be used are available commercially from the company BASF under the brand names Lupamin®: 1500, 4500, 4595, 9000, 9030, 9095. Amine-terminated polyether urethanes are available, for example, from Henkel under the brand names Loctite Liofol UR 9640.

Additional polyamines that may be used as component (B2) include highly branched polymers having amino groups, in particular primary amino groups on the branch termini.

A group of highly branched polymers that are particularly preferred as component (B2) includes the dendritic polymers, which are also referred to as dendrimers, cascade polymers or "starburst" polymers. These are understood to be synthetic macromolecules that are constructed step by step by linking two or more monomers with each monomer that has already been bound so that with each step the number of monomer end groups increases exponentially and at the end the result is a spherical tree structure. Preferred dendrimers include polyaminoamides (PAMAM) having primary amino functions on the branch ends. Those of the generation >0 are preferred. General 0 is understood to refer to dendrimers of the following structure:

[—CH$_2$N(CH$_2$CH$_2$CONHCH$_2$CH$_2$NH$_2$)$_2$]$_2$,

Especially preferred are dendrimers of the generation >1, wherein dendrimers of generation 1 have the following structure:

[—CH$_2$N[CH$_2$CH$_2$CONHCH$_2$CH$_2$N (CH$_2$CH$_2$CONHCH$_2$CH$_2$NH$_2$)$_2$]$_2$]$_2$ The structures of the higher generations, preferably up to generation 6, are derived from the above systematic creation of generation 0 to generation 1.

Dendrimers can be synthesized, for example, by stepwise reaction of ammonia or suitable representatives of the aforementioned alkylene diamines of the general formula R$^4$R$^5$N—Z—NR$^6$R$^7$ with acrylic acid esters. R$^4$—R$^7$ in these cases stands for hydrogen. Z is a linear or branched saturated or unsaturated alkylene chain with two or more carbon atoms. The polymer structure is created by Michael addition of the amino groups onto the olefinic double bonds and condensation of amino groups with ester groups. A suitable molar excess of amines is to be selected. Additional suitable amine components for the dendrimer structure can be found in the aforementioned groups of cycloalkylene diamines, diamines having both alkyl radical and cycloalkyl radicals and the group of amine-functionalized polyalkylene glycols. All the amine components in question have two primary amino functions in these cases.

Another preferred group of highly branched polymers that are used as component (B2) is formed, for example, by stepwise reaction of acrylic acid esters with suitable representatives of the aforementioned polyfunctional amines of the general formula H$_2$N—(CH$_2$CH$_2$—NH)X—CH$_2$CH$_2$—NH$_2$, where 1<x<10, such as diethylenetriamine, triethylenetetramine, tetraethylenepentamine and pentaethylenehexamine, for example.

The component (B2) that can be used according to the invention may also be synthesized by reaction of an excess of the aforementioned low-molecular polyfunctional amines that can be used as component (B1) with cyclic carbonates having an average molecular weight (Mw) of less than 1000 g/mol, preferably of 100 g/mol to 800 g/mol. In these cases, a suitable molar excess of amine in relation to the cyclocarbonate is to be selected so that, on the one hand, the desired molecular weight is achieved, while additionally the amine functionality according to the invention is present for use as component (B2).

Component (B2) is used as a single component or as a mixture of the corresponding compounds that can be used as component (B2).

The binder system described herein is suitable in particular as an adhesive/sealant.

The subject matter of the present invention is therefore also a method for synthesis of an adhesive/sealant using the binder system described herein, wherein component (A) is mixed with component (B) in a ratio of carbonate groups to primary amino groups of 30:1 to 0.2:1, preferably 10:1 to 0.4:1, more preferably from 5:1 to 0.5:1, especially preferably from 2:1 to 0.6:1 and most preferably approximately 1:1. If no primary amino groups are present in the molecule, then the ratio is to be applied to the secondary amino groups. The functional groups of components (A), (B1), (B2) are to be taken into account on the whole.

In a preferred embodiment of the method described herein, the reaction takes place between component (A) and component (B) in the presence of a solvent.

Fundamentally all solvents known to those skilled in the art may be used as the solvent here, in particular ketones, halogenated hydrocarbons, alkanes, alkenes and aromatic hydrocarbons. Examples of such solvents include methylene chloride, trichloroethylene, toluene, xylene, butyl acetate, amyl acetate, isobutyl acetate, methyl isobutyl ketone, methoxybutyl acetate, cyclohexane, cyclohexanone, dichlorobenzene, diethyl ketone, diisobutyl ketone, dioxane, ethyl acetate, ethylene glycol monobutyl ether acetate, ethylene glycol monoethyl acetate, 2-ethyihexylacetate, glycol diacetate, heptane, hexane, isobutyl acetate, isooctane, isopropyl acetate, methyl ethyl ketone, tetrahydrofuran or tetrachloroethylene or mixtures of two or more of the aforementioned solvents.

In a special embodiment of the method described herein, the reaction between component (A) and component (B) takes place with catalysis. To do so, catalytic amounts of a base are added to the mixture. Such bases and the amount to be used are described in U.S. Pat. No. 5,977,266 and WO 02/079148. Reference is made in particular to WO 98/50345, page 3, line 1 to page 4, line 17. However, the catalyst may also be already present in component (A) or (B). For adhesive bonding or sealing, at least one side of a substrate to be bonded or sealed is coated with the mixture and the side thereby coated is joined to at least one additional substrate.

The binder system described herein is suitable for adhesive bonding and sealing of a wide variety of substrates. These substrates include, for example, wood, metal, glass, plant fibers, stone, brick, paper, cellulose hydrate, plastics such as polystyrene, polyethylene, polypropylene polyethylene terephthalate, polyvinyl chloride, copolymers of vinyl chloride and vinylidene chloride, copolymers of vinyl acetate olefins, polyamides, in particular plastic films, metals, in particular films of aluminum, lead or copper.

The binder system described herein is particularly suitable as a two-component adhesive for adhesive bonding of paper, cardboard, wood, plastic, metal or masonry.

In a particularly preferred embodiment of the invention, the binder system described herein is used as a solvent-free or solvent-based lamination adhesive. The lamination adhesive is preferably essentially solvent-free, in particular essentially free of water.

The binder system described herein can be applied to the substrates to be bonded by using all conventional application methods, for example, by spraying, doctor application, three-four-roller application systems in the case of use of a solvent-free binder system or two-roller application systems in the case of use of a solvent-based binder system.

Due to its low viscosity, the binder system described herein is suitable in particular for adhesive binding of temperature-sensitive plastic films, for example, polyolefin films, in particular polyolefin films made of polyethylene or polypropylene.

Another subject matter of the present invention is therefore also a method for manufacturing film laminates that can be obtained by adhesive bonding of at least two plastic films that are the same or different over a partial area or the full area, using the binder system described herein. The binder system may be applied as a two-component adhesive to the films to be bonded using the machines conventionally used for such purposes, for example, traditional lamination machines. Another subject matter of the invention is a laminate film produced by the method described herein, using the binder system described herein. The laminated film is suitable in particular for packaging foods and luxury items as well as pharmaceutical drugs.

The binder system described herein may contain the usual additives such as plasticizers, silanes, antioxidants, UV stabilizers and antiaging agents. Plasticizers preferred for use here include phthalic acid esters, for example, dioctyl phthalate, ditridecyl phthalate and butylbenzyl phthalate, phosphoric acid esters such as, for example, tricresyl phosphate, adipates, for example, dioctyl adipate or benzoates, for example, propylene glycol dibenzoate.

Aminosilanes, epoxysilanes or mercaptosilanes, in particular γ-glycidyloxypropyl trimethoxysilane or γ-aminopropyl trimethoxysilane, are used in particular to improve adhesion to glass, metals, etc.

For use as a sealing compound, inorganic fillers such as carbon black, calcium carbonate, titanium dioxide and the like may be added to the binder systems described herein. Highly dispersed silicic acids, in particular pyrogenic silicic acids or precipitated silicic acids are preferably used as the inorganic fillers which have a thixotropic effect and whose thixotropic properties are also maintained in the binder systems described herein, even after prolonged storage.

For use as a lamination adhesive, the binder system is preferably free of inorganic fillers.

The invention will now be described below on the basis of a few exemplary embodiments. The amounts indicated are understood to be % by weight, unless otherwise indicated.

All the embodiments disclosed herein in conjunction with the binder system can of course also be used with the applications and methods described herein and vice versa.

EXAMPLES

Raw Materials:
PPG2000: Voranol 2000 L, propylene glycol, Mw=2000 g/mol, Dow
Lupranat MIS: diphenylmethane diisocyanate, isomer mixture, BASF
Glycerin carbonate: Jeffsol glycerin carbonate (4-hydroxymethyl-1,3-dioxolan-2-one), Huntsman
TIB Kat 216: dioctyltin dilaurate, TIB Chemicals
Epoxy 1: commercially available difunctional propylene glycol-based epoxy resin (EEW 320 g/mol)
Amine 1: commercially available difunctional amine with only primary amino groups, Mw=176 g/mol
Amine 2: commercially available hyperbranched polyethyleneimine (primary/secondary/tertiary amine ratio: 1/6.9/0.5), Mw=800 g/mol
Preparation of the Components:
Synthesis of the Solvent-free Prepolymer 1 (KA1)
PPG2000 (435.46 g) is placed in a three-neck flask, dehydrated (10 mbar, 80° C.) for 1 hour and aerated with nitrogen. After cooling and storing overnight under a protective gas, Lupranat MIS (104.69 g) was added, and after dissolving completely, the reaction mixture was adjusted to 80° C. again. NCO titrations are performed regularly and at NCO=2.91%, glycerin carbonate (46.30 g) is added at a lower temperature (50.6° C.). Immediately following that, 0.05% by weight TIB Kat 216 (0.30 g) was additionally added and after the exothermic reaction was finished, the reaction mixture was again heated to 80° C. until reaching NCO <0.1%.
Synthesis of the Solvent-Based Prepolymer 2 (KA2)
PPG2000 (1548.14 g) is placed in a three-neck flask, dehydrated (<10 mbar, 80° C.) for 1 hour and aerated with nitrogen. After cooling and storing overnight under a protective gas, the reaction mixture was adjusted immediately to approx. 34° C. and Lupranat MIS (371.92 g) was added. After complete homogenization, the reaction mixture is again set or 80° C. NCO titrations are carried out regularly and at NCO=3.01%, glycerin carbonate (164.69 g) is added at a lower temperature (50.2° C.). Immediately after that, 0.05% by weight TIB Kat 216 (0.30 g) was additionally added, and after the exothermic reaction was completed, the reaction mixture was again heated to 80° C. until reaching NCO<0.1%. Next at approx. 55° C., ethanol (1390.46 g) was added to achieve a solids content 60% by weight.

Component A with Epoxy (KA3)
KA1 (2100 g) was placed in a vessel and epoxy resin was added to epoxy 1 (176 g). The mixture was stirred with a wooden spatula until it was homogenized and was stored until use.

Preparation of the Curing Agent (KB1)
Amine 1 (20.00 g) and amine 2 (80.09 g) were mixed at one temperature using a magnetic stirrer until the mixture was homogenous.

Preparing the adhesives and laminations:
Preparation of the Solvent-Based Adhesive 1 and Lamination (KS1) (Comparative Example)
KA1 (11.00 g) was dissolved in ethyl acetate (35.4805 g). In addition KB1 (0.8268 g) was added (ratio of primary amine/cyclocarbonate=1/1-equivalent). This produces an adhesive that has a solids content of 25% by weight and can be laminated (KS1). KS1 was applied to a PET film using a spiral doctor applicator (0.08 mm), and the solvent was evaporated for 5 minutes at 90° C. in a drying cabinet. Immediately thereafter the lamination was completed with a PE film (surface corona pretreated) with the help of a laboratory lamination device. The laminate (2 to 3.5 g/m$^2$, dry) was stored at 40° C. under pressure (5 kg weight) and strips were cut off regularly to determine the laminate adhesion (15 mm wide strips, 90° peel tests on a tensile testing machine at 100 mm/min). An IR spectrum was recorded of the PE layer of laminate (ATR). Laminate adhesion after one day at 40° C.: PET/PE 0.72 N/15 mm, co-adhesive break, both strips still tacky. The IR spectrum after 3 days at 40° C. still had the cyclocarbonate carbonyl group band at 1818.30 cm$^{-1}$.

Preparing the Solvent-Based Adhesive 2 and Lamination (KS2) (According to the Invention)
KA3 (2276 g) was dissolved in ethanol (2330 g) and the curing agent KB1 (157 g) was added to it (ratio of primary amine/cyclocarbonate=1/1-equivalent) and homogenized using wooden spatula. The result was an adhesive containing 32% by weight solids which could be laminated (KS2). KS2 was applied by means of a laboratory combination lamination system with roller application (engraving roller with 50 lines per cm) and the parameters were adjusted so that the application weight (dry) was approx. 2.5 g/m$^2$. The laminated wound roll was stored at 40° C. immediately after lamination. Laminate adhesion after 1 day at 40° C.: PET/PE: 2.05 N/15 mm, adhesive break, PE still tacky. IR spectrum after 2 days at 40° C. no longer had a band for the cyclocarbonate carbonyl group at 1818.30 cm$^{-1}$.

The invention claimed is:
1. A two component binder system containing resin component (A) and curing agent component (B), wherein:
(i) Component (A) comprises at least one compound containing at least two cyclic carbonate groups and at least one compound containing at least two epoxy groups; and

(ii) Component (B) comprises: a first compound containing at least two (—NHR—) atomic groups and having a molecular weight of 60 g/mol to 500 g/mol, and a second compound containing at least two (—NHR—) atomic groups and having a molecular weight of greater than 500 g/mol, wherein R is H, an alkyl or aryl radical.

2. The binder system according to claim 1, wherein the at least one compound containing at least two cyclic carbonate groups is a polymer containing cyclic carbonate groups selected from the group consisting of optionally alkoxylated castor oil, optionally alkoxylated dimer diol, polyethers, polyether polyols, polyesters, polyester polyols, polycarbonates, polycarboxylic acids, polyacrylates, polymethacrylates, polyamides, polyamines, polyurethanes, and mixtures thereof.

3. The binder system according to claim 1, wherein the at least one compound containing at least two cyclic carbonate groups is a reaction product of cyclic hydroxyalkyl carbonate with a polymer containing isocyanate groups.

4. The binder system according to claim 1, wherein the at least one compound containing at least two cyclic carbonate groups is a reaction product of cyclic hydroxyalkyl carbonate having a five-membered or six-membered carbonate ring with a polymer containing isocyanate groups.

5. The binder system according to claim 1, wherein the at least one compound containing at least two cyclic carbonate groups is a reaction product of a glycerin carbonate with a polymer containing isocyanate groups.

6. The binder system according to claim 1, wherein the at least one compound containing at least two cyclic carbonate groups is a reaction product of cyclic hydroxyalkyl carbonate with an isocyanate group-terminated polyurethane prepolymer that is the reaction product of a polyol with an aromatic diisocyanate.

7. The binder system according to claim 1, wherein the at least one compound containing at least two cyclic carbonate groups is a reaction product of cyclic hydroxyalkyl carbonate with an isocyanate group-terminated polyurethane prepolymer that is the reaction product of a polyol with an average molecular weight Mw of 75 to 2000 g/mol with methylene diphenyl diisocyanate.

8. The binder system according to claim 1, wherein the compound containing at least two epoxy groups is an aliphatic epoxy.

9. The binder system according to claim 1, wherein the compound containing at least two epoxy groups is an aliphatic epoxy with an EEW of 120 to 350 g/mol.

10. The binder system according to claim 1, wherein the first and second compounds of Component (B) are:
(i) selected from the group consisting of alkylene diamines, cycloalkylene diamines, amine-functionalized polyalkylene glycols, and polyfunctional amines;
(ii) a polymer or a highly branched polymer or a dendrimer, selected from the group consisting of polyamines, polyimines, polyethers, polyamides, polyaminoamides, polyurethanes, polyolefins, polyvinyl amines, and mixtures thereof; or
(iii) a mixture of the compounds according to (i) and (ii).

11. A cured reaction product of a mixture comprising Component (A) and Component (B) of claim 1.

12. A two-component adhesive comprising the binder system of claim 1.

13. A two-component adhesive comprising the binder system of claim 1, wherein the adhesive is solvent-free.

14. A two-component adhesive comprising the binder system of claim 1, wherein the adhesive further comprises solvent.

15. A food package comprising a laminate of at least two films with the binder system of claim 1 disposed therebetween.

16. A food package comprising a laminate of at least two films bonded together by cured reaction products of an adhesive comprising the binder system of claim 1.

17. A method for producing an adhesive or sealant using the binder system of claim 1, comprising:
providing the binder system of claim 1;
mixing component (A) with component (B) in a ratio of carbonate groups to primary amino groups of 30:1 to 0.2:1, wherein the mixing ratio is to be applied to secondary amino groups in the absence of primary amino groups.

18. A method for producing an adhesive or sealant using the binder system of claim 1, comprising:
providing the binder system of claim 1;
mixing component (A) with component (B) in a ratio of carbonate groups to primary amino groups of 5:1 to 0.5:1, wherein the mixing ratio is to be applied to secondary amino groups in the absence of primary amino groups.

19. A method for producing an adhesive or sealant using the binder system of claim 1, comprising:
providing the binder system of claim 1; and
mixing component (A) with component (B) in a ratio of carbonate groups to primary amino groups of about 1:1, wherein the mixing ratio is to be applied to secondary amino groups in the absence of primary amino groups.

20. The binder system according to claim 1, wherein the first compound containing at least two (—NHR—) atomic groups has a molecular weight of 60 g/mol to 300 g/mol.

21. The binder system according to claim 20, wherein the second compound containing at least two (—NHR—) atomic groups has a molecular weight of 500 g/mol to 5,000,000 g/mol.

22. The binder system according to claim 21, wherein the second compound containing at least two (—NHR—) atomic groups has a molecular weight of 600 g/mol to 20,000 g/mol.

* * * * *